US012263304B1

(12) United States Patent
Hilliard

(10) Patent No.: US 12,263,304 B1
(45) Date of Patent: Apr. 1, 2025

(54) FACE MASK IMPREGNATED WITH MEDICINE

(71) Applicant: Jon E Hilliard, Gastonia, NC (US)

(72) Inventor: Jon E Hilliard, Gastonia, NC (US)

( * ) Notice: Subject to any disclaimer, the term of this patent is extended or adjusted under 35 U.S.C. 154(b) by 819 days.

(21) Appl. No.: 17/480,703

(22) Filed: Sep. 21, 2021

Related U.S. Application Data

(60) Provisional application No. 63/125,487, filed on Dec. 15, 2020.

(51) Int. Cl.

| | |
|---|---|
| ***A61M 16/06*** | (2006.01) |
| ***A45D 44/00*** | (2006.01) |
| ***A61M 35/00*** | (2006.01) |
| ***A62B 18/08*** | (2006.01) |
| ***A62B 23/02*** | (2006.01) |
| ***B01D 39/08*** | (2006.01) |

(52) U.S. Cl.

CPC ........... *A61M 16/06* (2013.01); *A45D 44/002* (2013.01); *A61M 35/10* (2019.05); *A62B 18/084* (2013.01); *A62B 23/025* (2013.01); *B01D 39/08* (2013.01); *B01D 2239/0478* (2013.01); *B01D 2239/0654* (2013.01)

(58) Field of Classification Search

CPC ..... A61M 16/06; A61M 35/10; A45D 44/002; A62B 18/084; A62B 23/025; B01D 39/08

See application file for complete search history.

(56) References Cited

U.S. PATENT DOCUMENTS

| | | | | |
|---|---|---|---|---|
| 4,252,119 A * | 2/1981 | Coates | A61F 15/001 604/306 |
| 4,372,318 A * | 2/1983 | Viesturs | A61F 7/02 607/109 |
| 4,516,564 A * | 5/1985 | Koiso | A61F 7/034 607/114 |
| 4,525,410 A * | 6/1985 | Hagiwara | A01N 59/16 424/641 |
| 4,790,307 A | 12/1988 | Haber | |
| 4,856,509 A | 8/1989 | Lemelson | |
| 5,948,010 A * | 9/1999 | Adamec | A61F 7/02 607/108 |
| 6,409,746 B1 * | 6/2002 | Igaki | A61F 7/03 607/114 |

(Continued)

FOREIGN PATENT DOCUMENTS

WO 2017184798 10/2017

*Primary Examiner* — Guy K Townsend

(74) *Attorney, Agent, or Firm* — Kyle A. Fletcher, Esq.

(57) ABSTRACT

The face mask impregnated with medicine is adapted for use with a patient. The face mask impregnated with medicine covers the mouth and nose on the face of the patient. The face mask impregnated with medicine filters the air that is inhaled and exhaled by the patient. The face mask impregnated with medicine removes particulates, including microorganisms, from the air that is inhaled and exhaled by the patient. The face mask impregnated with medicine comprises a mask structure, a fastening structure, and a medical coating. The mask structure filters the air that is inhaled and exhaled by the patient. The fastening structure attaches the mask structure to the patient. The medical coating is a pharmacologically active media that treats medical conditions that are caused or exacerbated by the mask structure.

14 Claims, 4 Drawing Sheets

103
111
112
113

(56) References Cited

U.S. PATENT DOCUMENTS

| | | | | |
|---|---|---|---|---|
| 6,537,308 | B2 * | 3/2003 | Burkhart | A61F 7/02 604/303 |
| 6,823,860 | B2 * | 11/2004 | Igaki | A61F 7/03 126/263.05 |
| 6,824,786 | B2 * | 11/2004 | Yu | A61K 31/205 514/567 |
| 7,452,545 | B2 * | 11/2008 | Yu | A61P 17/00 514/557 |
| 7,559,907 | B2 * | 7/2009 | Krempel | A61F 7/103 602/5 |
| 7,652,228 | B2 * | 1/2010 | Igaki | A61F 7/034 424/443 |
| 7,802,572 | B2 | 9/2010 | Hahne | |
| 7,976,573 | B2 * | 7/2011 | Korb | A61H 7/00 604/294 |
| 7,981,147 | B2 * | 7/2011 | Korb | A61H 7/00 604/289 |
| 8,034,092 | B2 * | 10/2011 | Bruder | A61F 13/00063 607/108 |
| 8,343,203 | B2 * | 1/2013 | Ishikawa | A61F 7/034 424/443 |
| 8,357,189 | B2 * | 1/2013 | Ugajin | C09K 5/18 607/108 |
| 8,420,882 | B2 * | 4/2013 | Bruder | A61F 13/00063 |
| 8,524,973 | B2 * | 9/2013 | Bruder | A61F 13/0226 602/53 |
| 8,535,363 | B1 * | 9/2013 | Lewis | A61F 7/007 219/528 |
| 8,636,786 | B2 * | 1/2014 | Biser | A61F 7/02 607/107 |
| 8,784,391 | B1 * | 7/2014 | Biser | A61F 7/02 604/294 |
| 8,999,300 | B2 * | 4/2015 | Iwama | A61K 9/0014 424/59 |
| 9,445,939 | B2 * | 9/2016 | Bruder | A61F 13/0203 |
| 9,561,255 | B2 * | 2/2017 | Iwama | A61K 9/06 |
| 9,592,149 | B2 * | 3/2017 | Hidaka | A61F 7/034 |
| 9,629,401 | B2 | 4/2017 | Malki | |
| 9,642,740 | B2 * | 5/2017 | Bruder | A61L 15/44 |
| 9,719,977 | B2 * | 8/2017 | Korb | A61H 9/0057 |
| 9,724,230 | B2 * | 8/2017 | Badawi | A61H 23/0245 |
| 9,925,087 | B2 * | 3/2018 | Bruder | A61F 13/01021 |
| 10,105,259 | B2 * | 10/2018 | Bruder | A61F 13/00 |
| D844,795 | S * | 4/2019 | Bruder | D24/206 |
| 10,314,346 | B2 * | 6/2019 | Potnis | A41D 13/0056 |
| D870,906 | S * | 12/2019 | Bruder | D24/206 |
| D871,598 | S * | 12/2019 | Bruder | D24/206 |
| 10,544,181 | B2 * | 1/2020 | Ono | A61Q 1/02 |
| 2002/0032153 | A1 * | 3/2002 | Whitehouse | A61K 38/1825 514/8.1 |
| 2003/0167556 | A1 * | 9/2003 | Kelley | A45D 44/002 2/206 |
| 2003/0208150 | A1 * | 11/2003 | Bruder | A61F 13/00 602/48 |
| 2004/0163649 | A1 | 8/2004 | Shao | |
| 2004/0180854 | A1 * | 9/2004 | Yu | A61K 31/122 514/54 |
| 2005/0118383 | A1 * | 6/2005 | Cargill | A61F 7/02 428/36.1 |
| 2005/0278008 | A1 * | 12/2005 | Ladmer | A61F 7/02 607/114 |
| 2006/0182788 | A1 * | 8/2006 | Singh | A61L 15/44 424/448 |
| 2007/0044801 | A1 * | 3/2007 | Mathis | B32B 5/26 128/206.13 |
| 2008/0251081 | A1 * | 10/2008 | Claussen | A41D 13/1192 128/205.27 |
| 2009/0104243 | A1 * | 4/2009 | Utkhede | A61F 9/0017 424/423 |
| 2009/0287282 | A1 * | 11/2009 | Biser | A61F 7/02 607/109 |
| 2009/0287283 | A1 * | 11/2009 | Biser | A61F 7/02 607/109 |
| 2010/0106109 | A1 * | 4/2010 | Bruder | A61L 15/42 604/290 |
| 2010/0312317 | A1 * | 12/2010 | Baltazar | A61F 7/02 607/108 |
| 2011/0091403 | A1 * | 4/2011 | Yu | A61K 31/7004 514/20.7 |
| 2011/0208279 | A1 * | 8/2011 | Sanker | A61F 7/02 607/109 |
| 2011/0307041 | A1 * | 12/2011 | Floyd | A61F 7/10 523/105 |
| 2012/0053537 | A1 * | 3/2012 | Bruder | A61F 13/00 604/290 |
| 2012/0258059 | A1 * | 10/2012 | Iwama | A61K 8/64 424/59 |
| 2013/0084305 | A1 * | 4/2013 | Iwama | A61K 31/715 424/195.18 |
| 2013/0131613 | A1 * | 5/2013 | Elkins | A61F 9/04 604/303 |
| 2013/0245578 | A1 * | 9/2013 | Bruder | A61F 7/02 607/114 |
| 2013/0317459 | A1 * | 11/2013 | Bruder | A61F 13/00063 604/290 |
| 2013/0317460 | A1 * | 11/2013 | Bruder | A61L 15/44 604/291 |
| 2014/0186420 | A1 * | 7/2014 | Utkhede | A61P 27/02 514/530 |
| 2014/0277303 | A1 * | 9/2014 | Biser | A61F 7/02 607/104 |
| 2014/0288624 | A1 * | 9/2014 | Wasko | A61F 7/02 607/109 |
| 2014/0330222 | A1 * | 11/2014 | Bruder | A61F 13/124 604/290 |
| 2015/0088236 | A1 * | 3/2015 | Bruder | A61F 13/01021 607/108 |
| 2016/0120692 | A1 * | 5/2016 | Chen | A61F 7/03 607/109 |
| 2016/0206476 | A1 * | 7/2016 | Robertson | A61F 9/045 |
| 2017/0049614 | A1 * | 2/2017 | Paulson | A61F 9/04 |
| 2017/0216088 | A1 * | 8/2017 | Johnson | A61F 7/02 |
| 2017/0252210 | A1 * | 9/2017 | Bruder | A61F 9/045 |
| 2017/0266035 | A1 * | 9/2017 | Kuo | G08C 17/02 |
| 2017/0266053 | A1 * | 9/2017 | Rodriguez | A61F 13/124 |
| 2017/0312121 | A1 * | 11/2017 | Bruder | A61F 13/00 |
| 2018/0289531 | A1 * | 10/2018 | Thomas | A61F 7/007 |
| 2018/0338864 | A1 * | 11/2018 | Paulson | A61F 7/007 |
| 2019/0000666 | A1 * | 1/2019 | Bruder | A61F 13/00063 |
| 2019/0053940 | A1 * | 2/2019 | Biser | A61F 7/0241 |
| 2019/0069611 | A1 * | 3/2019 | Potnis | A41D 13/0053 |
| 2019/0083299 | A1 * | 3/2019 | Rozanski | A61F 7/02 |
| 2019/0125579 | A1 * | 5/2019 | Habib | A61F 9/04 |
| 2019/0126585 | A1 | 5/2019 | Potnis et al. | |
| 2019/0159929 | A1 * | 5/2019 | Bruder | A61F 9/04 |
| 2019/0183671 | A1 * | 6/2019 | Baltazar | C09K 5/10 |
| 2019/0216639 | A1 * | 7/2019 | Bruder | A61F 7/02 |
| 2020/0337893 | A1 * | 10/2020 | Bruder | A61F 7/02 |
| 2021/0267793 | A1 * | 9/2021 | Bruder | A61F 7/02 |
| 2024/0081440 | A1 * | 3/2024 | O'Leary | A41D 13/1176 |

* cited by examiner

FIG. 1
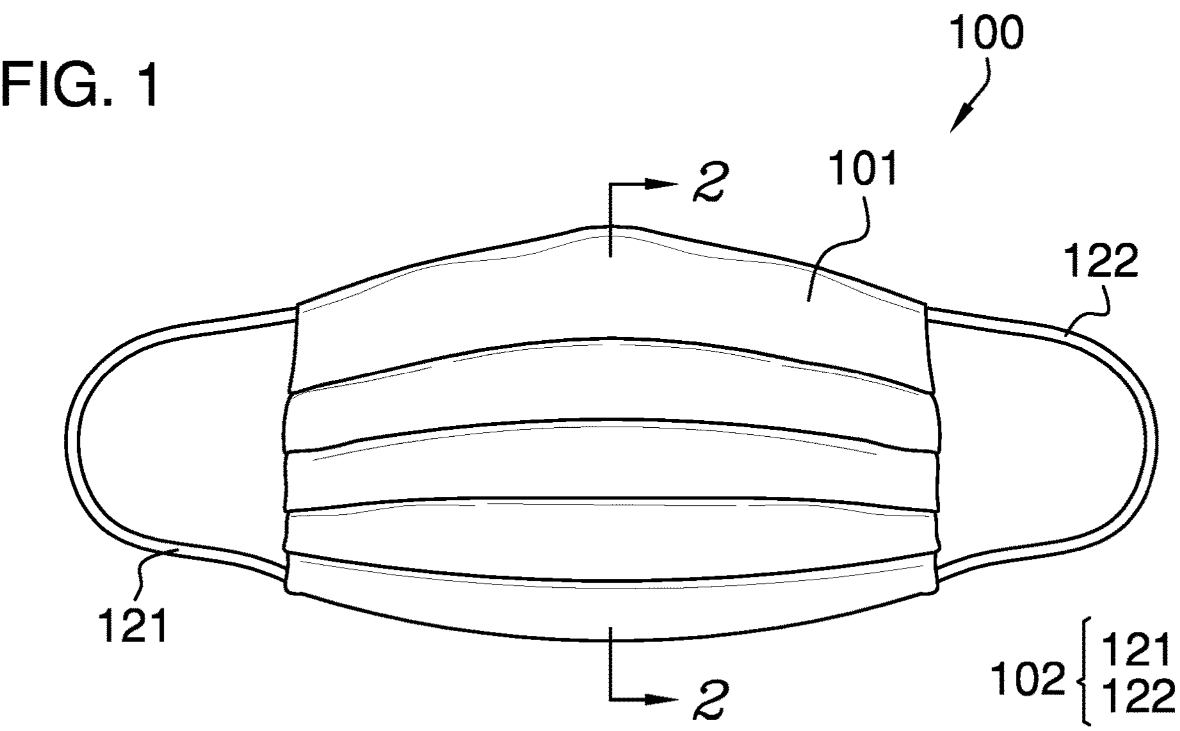
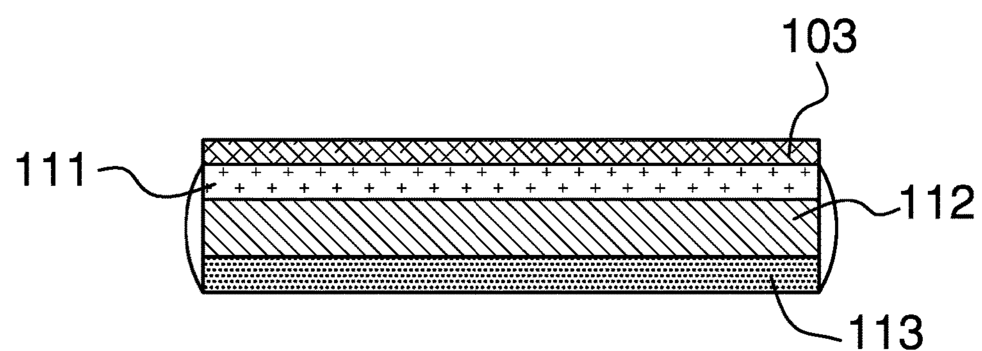
FIG. 2

CAS 302-79-4

CAS 18559-94-9

FACE MASK IMPREGNATED WITH MEDICINE

CROSS REFERENCES TO RELATED APPLICATIONS

This non-provisional application claims priority under 35 USC 119 (e) to United States provisional application U.S. 63/1,254,587 filed on Dec. 15, 2020 by the inventor: Jon E. Hilliard. This non-provisional application claims United States provisional application U.S. 63/1,254,587 in its entirety.

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of outerwear and protective garments, more specifically, a protective face mask. (A41D13/1115)

A virus is a microorganism. A virus comprises a nucleic acid and a protein shell. The protein shell forms a containment structure for the nucleic acid structure. In this disclosure, the virus is assumed to be a poison or, more specifically, a toxin. The terms poison and toxin are defined elsewhere in this disclosure. The virus is a biochemical structure that "infects" a host cell. By infecting a host cell is meant that the virus deposits the nucleic acid structure in the host cell such that the energy produced by the biochemical processes within the host cell is diverted towards the replication of the nucleic acid structure of the virus. An evolved virus refers to a virus that further comprises an envelope. The envelope is a lipid based structure that is similar to a cell membrane. The envelope encloses and protects the nucleic acid structure and the protein shell. The virus is defined elsewhere in this disclosure.

SUMMARY OF INVENTION

The face mask impregnated with medicine is adapted for use with a patient. The face mask impregnated with medicine covers the mouth and nose on the face of the patient. The face mask impregnated with medicine filters the air that is inhaled and exhaled by the patient. The face mask impregnated with medicine removes particulates, including microorganisms, from the air that is inhaled and exhaled by the patient. The face mask impregnated with medicine comprises a mask structure, a fastening structure, and a medical coating. The mask structure filters the air that is inhaled and exhaled by the patient. The fastening structure attaches the mask structure to the patient.

The medical coating is a pharmacologically active media that treats medical conditions that are caused or exacerbated by the mask structure.

These together with additional objects, features and advantages of the face mask impregnated with medicine will be readily apparent to those of ordinary skill in the art upon reading the following detailed description of the presently preferred, but nonetheless illustrative, embodiments when taken in conjunction with the accompanying drawings.

In this respect, before explaining the current embodiments of the face mask impregnated with medicine in detail, it is to be understood that the face mask impregnated with medicine is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the face mask impregnated with medicine.

It is therefore important that the claims be regarded as including such equivalent construction insofar as they do not depart from the spirit and scope of the face mask impregnated with medicine. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

FIG. 1 is a front view of an embodiment of the disclosure.

FIG. 2 is a cross-sectional view of an embodiment of the disclosure across 2-2 as shown in FIG. 1.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 3:
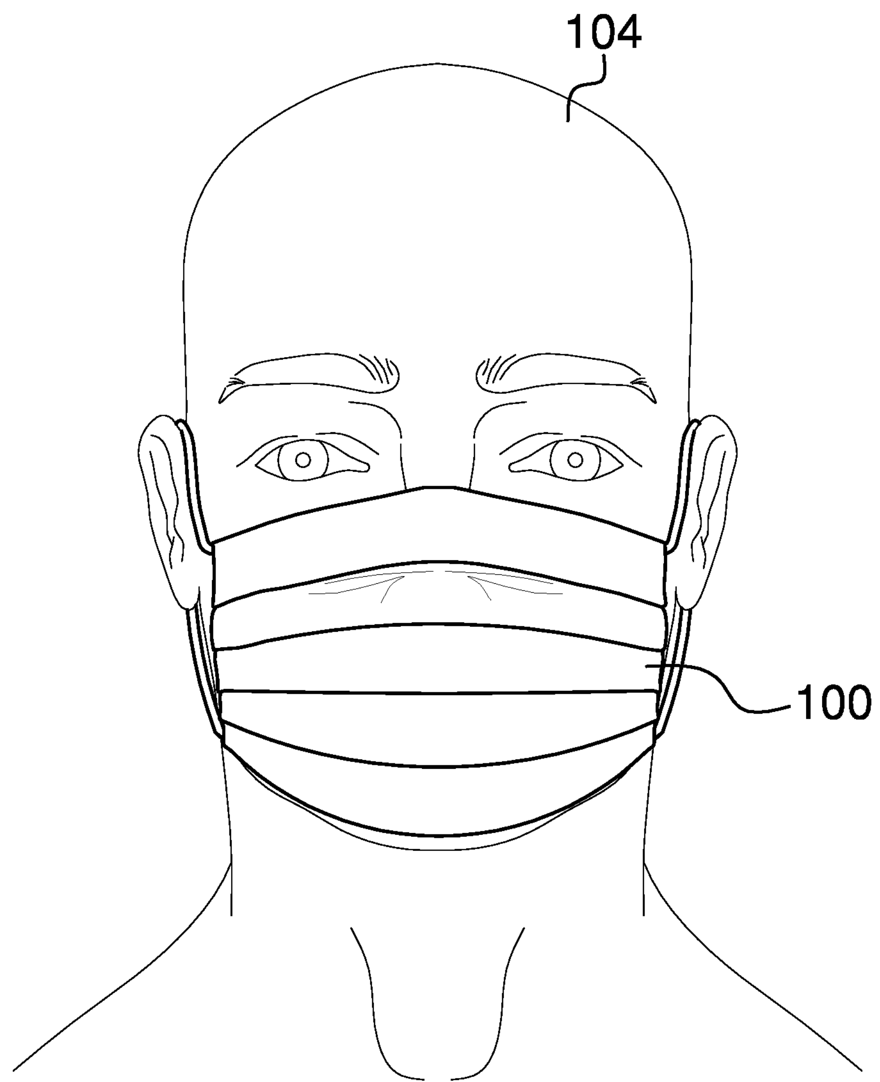
FIG. 3 is an in-use view of an embodiment of the disclosure.
Figure 4:
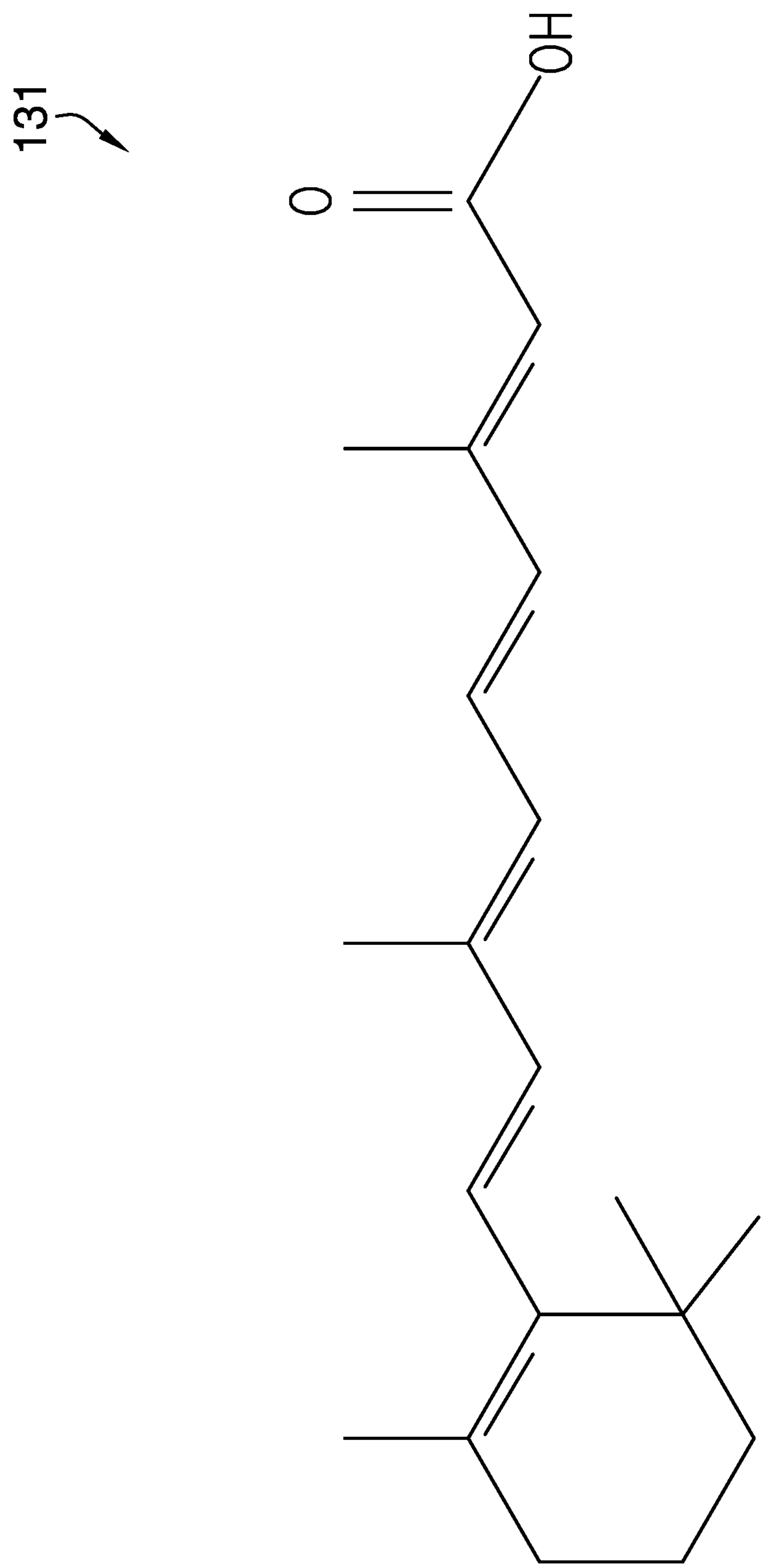
FIG. 4 is a detail view of an embodiment of the disclosure.
Figure 5:
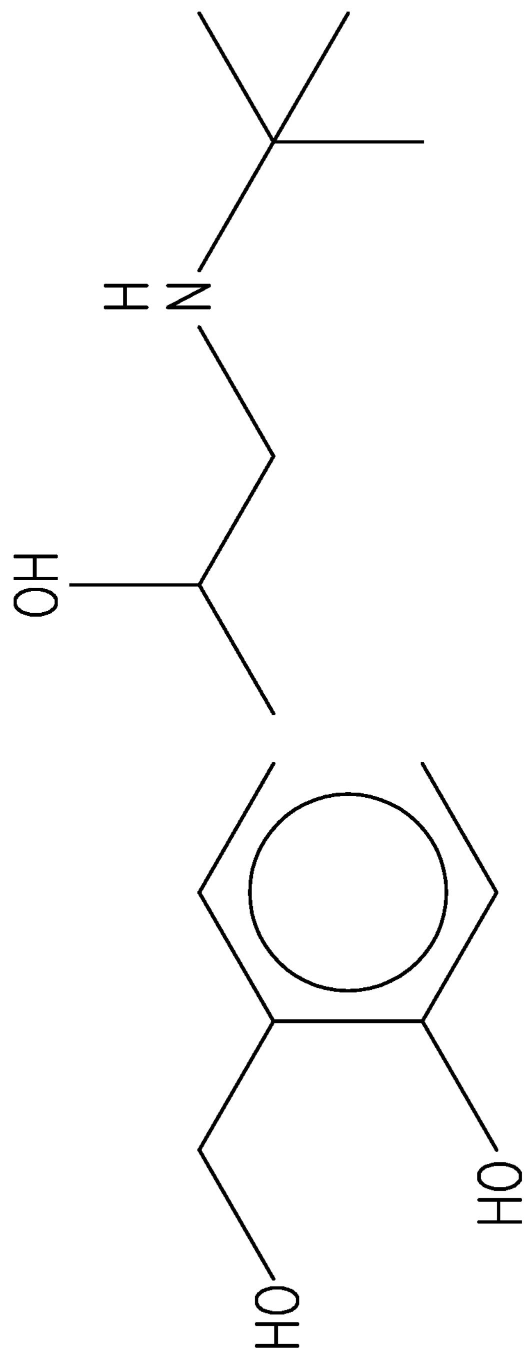
FIG. 5 is a detail view of an embodiment of the disclosure.

Detailed reference will now be made to one or more potential embodiments of the disclosure, which are illustrated in FIGS. 1 through 5.

The face mask impregnated with medicine 100 (hereinafter invention) is adapted for use with a patient 104. The invention 100 covers the mouth and nose on the face of the patient 104. The invention 100 filters the air that is inhaled and exhaled by the patient 104. The invention 100 removes particulates, including microorganisms, from the air that is inhaled and exhaled by the patient 104. The invention 100 comprises a mask structure 101, a fastening structure 102, and a medical coating 103. The mask structure 101 filters the air that is inhaled and exhaled by the patient 104. The fastening structure 102 attaches the mask structure 101 to the patient 104. The medical coating 103 is a pharmacologically active media that treats medical conditions that are caused or exacerbated by the mask structure 101. The patient 104 is defined elsewhere in this disclosure.

The mask structure 101 forms the filter of the invention 100. The mask structure 101 encloses the mouth and the nose of the patient 104. The mask structure 101 filters the air that is inhaled and exhaled by the patient 104. The mask structure 101 is a textile based structure. The mask structure 101 is a composite textile. The mask structure 101 comprises an inner layer 111, a filter layer 112, and an outer layer 113.

The inner layer 111 is a sheeting structure. The inner layer 111 is a textile based structure. The inner layer 111 is the layer of the composite prism structure of the mask structure 101 that is proximal to the face of the patient 104. The inner layer 111 is a gas permeable structure. The medical coating 103 is applied to the face of the inner layer 111 that is proximal to the face of the patient 104. The inner layer 111 is an absorbent structure that absorbs liquid droplets that are exhaled by the patient 104.

The outer layer 113 is a sheeting structure. The outer layer 113 is a textile based structure. The outer layer 113 is the layer of the composite prism structure of the mask structure 101 that is distal from the face of the patient 104. The outer layer 113 is a gas permeable structure. The outer layer 113 is an absorbent structure that absorbs liquid droplets that are exhaled by the patient 104.

The filter layer 112 is a sheeting structure. The filter layer 112 is a textile based structure. The filter layer 112 is a gas permeable structure. The filter layer 112 forms a filter that removes particulates, including microorganisms such as viruses, from the air that passes through the mask structure 101. The filter layer 112 is sandwiched between the inner layer 111 and the outer layer 113. In the first potential embodiment of the disclosure, the applicant prefers that the filter layer 112 forms an N95 filter.

The fastening structure 102 is a mechanical structure. The fastening structure 102 attaches to the mask structure 101. The fastening structure 102 secures the mask structure 101 to the head of the patient 104. The fastening structure 102 is an elastic structure. The fastening structure 102 comprises a first elastic cord 121 and a second elastic cord 122.

The first elastic cord 121 is an elastic cord. The elastic cord is defined elsewhere in this disclosure. The ends of the first elastic cord 121 attach to the mask structure 101. The first elastic cord 121 binds the mask structure 101 to the head of the patient 104.

The first elastic cord 121 acts as a spring. Specifically, when a force is applied to both ends of the first elastic cord 121 in a direction parallel to the center axis of the first elastic cord 121, the applied force elongates the span of the end to end length the first elastic cord 121 in the direction parallel to the center axis of the first elastic cord 121. The elasticity of the first elastic cord 121 creates a force that opposes the displacement created by the applied force. The elasticity of the first elastic cord 121 returns the first elastic cord 121 to its relaxed shape. When the elongated first elastic cord 121 is looped around an ear of the patient 104, the ear of the patient 104 will prevent the first elastic cord 121 from returning to its relaxed shape. In this circumstance, the first elastic cord 121 will apply a force projecting radially away from the center axis of the first elastic cord 121 and through the lateral face of the first elastic cord 121 and against the ear of the patient 104. This force binds the first elastic cord 121 to the ear of the patient 104.

The second elastic cord 122 is an elastic cord. The elastic cord is defined elsewhere in this disclosure. The ends of the second elastic cord 122 attach to the mask structure 101. The second elastic cord 122 binds the mask structure 101 to the head of the patient 104.

The second elastic cord 122 acts as a spring. Specifically, when a force is applied to both ends of the second elastic cord 122 in a direction parallel to the center axis of the second elastic cord 122, the applied force elongates the span of the end to end length the second elastic cord 122 in the direction parallel to the center axis of the second elastic cord 122. The elasticity of the second elastic cord 122 creates a force that opposes the displacement created by the applied force. The elasticity of the second elastic cord 122 returns the second elastic cord 122 to its relaxed shape. When the elongated second elastic cord 122 is looped around an ear of the patient 104, the ear of the patient 104 will prevent the second elastic cord 122 from returning to its relaxed shape. In this circumstance, the second elastic cord 122 will apply a force projecting radially away from the center axis of the second elastic cord 122 and through the lateral face of the second elastic cord 122 and against the ear of the patient 104. This force binds the second elastic cord 122 to the ear of the patient 104.

The medical coating 103 is a pharmacologically active media. The medical coating 103 is applied as a coating to the face of the inner layer 111 that is proximal to the face of the patient 104. The medical coating 103 is formed as a gas permeable structure. The medical coating 103 is selected from the group consisting of a topically applied pharmacologically active media and an inhaled pharmacologically active media. The medical coating 103 is selected to treat a condition that is caused or exacerbated by the use of the mask structure 101.

In the first potential embodiment of the disclosure, the medical coating 103 is selected from the group consisting of: a) a pharmacologically active media with a primary chemical structure of (all-trans)-3,7-dimethyl-9-(2,6,6-trimethyl-1-cyclohexene-1-yl)-2,4,6,8-nonatetraenoic acid (CAS 302-79-4) 131; and, b) a pharmacologically active media with a primary chemical structure of α-[[(1,1-Dimethylethyl) amino]methyl]-4-hydroxy-1,3-benzenedimethanol (CAS 18559-94-9) 132.

The (all-trans)-3,7-dimethyl-9-(2,6,6-trimethyl-1-cyclohexene-1-yl)-2,4,6,8-nonatetraenoic acid (CAS 302-79-4) 131 is a pharmacologically active media. The (all-trans)-3,7-dimethyl-9-(2,6,6-trimethyl-1-cyclohexene-1-yl)-2,4,6,8-nonatetraenoic acid (CAS 302-79-4) 131 is a topically applied to the patient 104. The (all-trans)-3,7-dimethyl-9-(2,6,6-trimethyl-1-cyclohexene-1-yl)-2,4,6,8-nonatetraenoic acid (CAS 302-79-4) 131 is a lipid that dissolves into the naturally occurring oils on the face of the patient 104. The (all-trans)-3,7-dimethyl-9-(2,6,6-trimethyl-1-cyclohexene-1-yl)-2,4,6,8-nonatetraenoic acid (CAS 302-79-4) 131 is commonly used to treat acne conditions. The (all-trans)-3,7-dimethyl-9-(2,6,6-trimethyl-1-cyclohexene-1-yl)-2,4,6,8-nonatetraenoic acid (CAS 302-79-4) 131 is defined elsewhere in this disclosure.

The 1,3-benzenedimethanol, α-[[(1,1-Dimethylethyl) amino]methyl]-4-hydroxy-1,3-benzenedimethanol (CAS 18559-94-9) 132 is a pharmacologically active media. The 1,3-benzenedimethanol, α1-[[(1,1-dimethylethyl)amino] methyl]-4-hydroxy-(CAS 18559-94-9) 132 is inhaled by the patient 104. The 1,3-benzenedimethanol, α1-[[(1,1-dimethylethyl)amino]methyl]-4-hydroxy-(CAS 18559-94-9) 132 is commonly used to treat asthma. The 1,3-benzenedimethanol, α1-[(1,1-dimethylethyl)amino]methyl]-4-hydroxy-(CAS 18559-94-9) 132 is defined elsewhere in this disclosure.

In the first potential embodiment of the disclosure, the intent of the applicant is to protect that patient 104 against a virus such as the COVID-19 virus. A virus is a microorganism. A virus comprises a nucleic acid and a protein shell. The protein shell forms a containment structure for the nucleic acid structure. In this disclosure, the virus is assumed to be a poison or, more specifically, a toxin. The terms poison and toxin are described elsewhere in this disclosure. The virus is a biochemical structure that "infects" a host cell. By infecting a host cell is meant that the virus deposits the nucleic acid structure in the host cell such that the energy produced by the biochemical processes within the host cell is diverted towards the replication of the nucleic acid structure of the virus. An evolved virus refers to a virus that further comprises an envelope. The envelope is a lipid based structure that is similar to a cell membrane. The envelope encloses and protects the nucleic acid structure and the protein shell. The virus is defined elsewhere in this disclosure. The COVID-19 virus is defined elsewhere in this disclosure.

The following definitions were used in this disclosure:

Absorbent: As used in this disclosure, absorbent is an adjective that refers to a material that is able to soak up a liquid such as water.

Albuterol: As used in this disclosure, albuterol (CAS 18559-94-9) refers to the chemical structure: α-[[(1,1-Dimethylethyl)amino]methyl]-4-hydroxy-1,3-benzenedimethanol. Albuterol is a pharmacologically active media. Albuterol is used to treat asthma. Albuterol is typically inhaled. Albuterol is also known as salbutamol.

Bind: As used in this disclosure, to bind is a verb that means to tie or secure a first object to a second object using a strap, cord or webbing.

Biochemistry: As used in this disclosure, biochemistry refers to the chemical substances and the chemical processes associated with biological processes.

Center: As used in this disclosure, a center is a point that is: 1) the point within a circle that is equidistant from all the points of the circumference; 2) the point within a regular polygon that is equidistant from all the vertices of the regular polygon; 3) the point on a line that is equidistant from the ends of the line; 4) the point, pivot, or axis around which something revolves; or, 5) the centroid or first moment of an area or structure. In cases where the appropriate definition or definitions are not obvious, the fifth option should be used in interpreting the specification.

Center Axis: As used in this disclosure, the center axis is the axis of a cylinder or a prism. The center axis of a prism is the line that joins the center point of the first congruent face of the prism to the center point of the second corresponding congruent face of the prism. The center axis of a pyramid refers to a line formed through the apex of the pyramid that is perpendicular to the base of the pyramid. When the center axes of two cylinder, prism or pyramidal structures share the same line they are said to be aligned. When the center axes of two cylinder, prism or pyramidal structures do not share the same line they are said to be offset.

Coating: As used in this disclosure, a coating refers to a substance that is applied to the exterior surface of an object such that the coating forms a new exterior surface of the object. A coating is commonly said to be formed as a layer. Paint is an example of a common coating material.

Composite Textile: As used in this disclosure, a composite textile is a multilayer fabric made of two or more joined layers of textile or sheeting materials.

Cord: As used in this disclosure, a cord is a long, thin, flexible, and prism shaped string, webbing, line, rope, or wire. Cords are made from yarns, piles, or strands of material that are braided or twisted together or from a monofilament (such as fishing line). Cords have tensile strength but are too flexible to provide compressive strength and are not suitable for use in pushing objects. String, line, cable, and rope are synonyms for cord.

COVID-19: As used in this disclosure, COVID-19 is a virus that is highly contagious between humans. The COVID-19 virus is also known as the severe acute respiratory syndrome coronavirus 2 (SARS-COV-2). The COVID-19 is responsible for the COVID-19 pandemic of 2020. The COVID-19 is an evolved virus. The COVID-19 has a diameter a range of between 50 and 200 nanometers.

This disclosure assumes that a representative diameter for COVID-19 is 100 nanometers. As of the writing of this definition, the environmental stability (the half-life survival time of the virus outside of the host) is between one and ten hours. See Virus Disk: As used in this disclosure, a disk is a prism-shaped object that is flat in appearance. The disk is formed from two congruent ends that are attached by a lateral face. The sum of the surface areas of two congruent ends of the prism-shaped object that forms the disk is greater than the surface area of the lateral face of the prism-shaped object that forms the disk.

In this disclosure, the congruent ends of the prism-shaped structure that forms the disk are referred to as the faces of the disk.

Dissolve: As used in this disclosure, to dissolve refers to the incorporation of a solute into a solvent to form a solution.

Dose: As used in this disclosure, the term dose refers to a specified measured quantity of a chemical substance that is to be incorporated or introduced into an organism or a mixture such as a recipe or a solution. The term dose often, but not necessarily, implies the introduction of a therapeutic substance or a pharmacologically active media into a patient.

Elastic: As used in this disclosure, an elastic is a material or object that deforms when a force is applied to it and that is able to return to its relaxed shape after the force is removed. A material that exhibits these qualities is also referred to as an elastomeric material. A material that does not exhibit these qualities is referred to as inelastic or an inelastic material.

Elastic Cord: As used in this disclosure, an elastic cord is a cord that contains elastic yarns as some of the yarns that make up the cord. An elastic cord is constructed such that the elastic cord will stretch when a force is applied and will return to its original shape when after the force is removed. Shock cord and bungee cord are synonyms for elastic cord.

Elastic Webbing: As used in this disclosure, an elastic webbing is a webbing that contains elastic yarns as some of the yarns that make up the webbing. An elastic webbing is constructed such that the elastic webbing will stretch when a force is applied and will return to its original shape when after the force is removed.

Face: As used in this disclosure, the face is the anterior portion of the head formed from the inferior surface of the mandible to the center of the frontal bone of the skull. The eyes, nose, and mouth of a person are located in the face.

Filter: As used in this disclosure, a filter is a mechanical device that is used to separate solids that are suspended in a liquid or a gas. A strainer is type of filter with what would be considered a coarse mesh measurement.

Fluid: As used in this disclosure, a fluid refers to a state of matter wherein the matter is capable of flow and takes the shape of a container it is placed within. The term fluid commonly refers to a liquid or a gas.

Gas: As used in this disclosure, a gas refers to a state (phase) of matter that is fluid and that fills the volume of the structure that contains it. Stated differently, the volume of a gas always equals the volume of its container.

Lipid: As used in this disclosure, a lipid is an organic molecule that is soluble in nonpolar solvents.

Liquid: As used in this disclosure, a liquid refers to a state (phase) of matter that is fluid and that maintains, for a given pressure, a fixed volume that is independent of the volume of the container.

Mask: As used in this disclosure, a mask is a covering for the face of a person. A mask filters air as it passes through the nose and mouth of a patient.

Microorganism: As used in this disclosure, a microorganism is an organism too small to be viewed by the unaided eye.

Microorganisms are typically single celled organisms such as bacteria, yeast, viruses, protozoa, fungi and algae. A pathogen refers to a microorganism that has the potential to cause illness or disease.

N95 Filter: As used in this disclosure, an N95 filter is a surface filter designed to remove particulates from an air flow. The established performance standard for the N95 filter requires that the N95 filter be capable of removing 95% of the particulates having a diameter of greater than or equal to 300 nanometers from the air flow. As a practical matter, most N95 filters remove over 99% (a published estimate that was current as this definition is written has 99.8%) of the particulates having a diameter of greater than or equal to 100 nanometers from the air flow. An N95 respirator, or less formally an N95 mask, is a respirator that filters the flow of breathing air through an N95 filter. An N99 filter is rated as removing over 99% of the particulates having a diameter of greater than or equal to 300 nanometers from the air flow.

Non-Polar Molecule: As used in this disclosure, a non-polar molecule refers to a molecular structure that: a) is electrically neutral; and, b) has a uniform spatial distribution of the electrons within the molecule.

Patient: As used in this disclosure, a patient is a person who is designated to receive a medical treatment, therapy or service. The term patient may be extended to an animal when used within the context of the animal receiving veterinary treatment or services.

Pharmacologically Active Media: As used in this disclosure, a pharmacologically active media refers to a chemical substance that has a biochemical or physiological effect on a biological organism.

Polar Molecule: As used in this disclosure, a polar molecule refers to a molecular structure that: a) is electrically neutral; but, b) does not have a uniform spatial distribution of the electrons within the molecule. A polar molecule will present one or more electrically positive poles and the same number of electrically negative poles within the molecular structure.

Polarity: As used in this disclosure, the term polarity is used to describe a physical property or physical characteristic wherein: 1) the physical property or physical characteristic manifests two opposing attributes, tendencies, characteristics, or principals; and, 2) the two opposing attributes, tendencies, characteristics, or principals have an intrinsic separation, alignment, or orientation.

Poison: As used in this disclosure, a poison is a chemical substance that interferes with the normal biological processes of a biological organism. The term poison often implies the injury to or death of the biological organism. A toxin is a poison that generates an immune system response.

Primary Chemical Structure: As used in this disclosure, a primary chemical structure refers to a family of chemical structures that: a) share a common chemical structure; and that, b) are differentiated by differences in the one or more functional that are attached to the primary chemical structure.

Prism: As used in this disclosure, a prism is a three-dimensional geometric structure wherein: 1) the form factor of two faces of the prism are congruent; and, 2) the two congruent faces are parallel to each other. The two congruent faces are also commonly referred to as the ends of the prism. The surfaces that connect the two congruent faces are called the lateral faces. In this disclosure, when further description is required a prism will be named for the geometric or descriptive name of the form factor of the two congruent faces. If the form factor of the two corresponding faces has no clearly established or well-known geometric or descriptive name, the term irregular prism will be used. The center axis of a prism is defined as a line that joins the center point of the first congruent face of the prism to the center point of the second corresponding congruent face of the prism. The center axis of a prism is otherwise analogous to the center axis of a cylinder. A prism wherein the ends are circles is commonly referred to as a cylinder.

Relaxed Shape: As used in this disclosure, a structure is considered to be in its relaxed state when no shear, strain, or torsional forces are being applied to the structure.

Retinoic Acid: As used in this disclosure, retinoic acid (CAS 302-79-4) refers to the chemical structure: (all-trans)-3,7-Dimethyl-9-(2,6,6-trimethyl-1-cyclohexene-1-yl)-2,4,6,8-nonatetraenoic acid. Retinoic acid is a pharmacologically active media. Retinoic acid is a lipid soluble structure. Retinoic acid is applied topically to treat skin conditions such as acne Sandwich: As used in this disclosure, to sandwich means to insert a first disk-shaped structure between a second disk-shaped structure and a third disk-shaped structure to form a composite prism structure. Specifically: a) a first congruent end of the first disk-shaped structure is placed against a first interior congruent end of the second disk-shaped structure; and, b) a second congruent end of the first disk-shaped structure is placed against a second interior congruent end of the third disk-shaped structure. A first exterior congruent end of the second disk-shaped structure forms a first overall congruent end of the overall composite prism structure described in this definition. A second exterior congruent end of the third disk-shaped structure forms a second overall congruent end of the overall composite prism structure described in this definition. The second overall congruent end of the overall composite prism structure is distal from the first overall congruent end. The verb to sandwich describes the act of placing the second disk-shaped structure between the first disk-shaped structure and the third disk-shaped structure.

Sheeting: As used in this disclosure, a sheeting is a material, such as a paper, textile, a plastic, or a metal foil, in the form of a thin flexible layer or layers. The sheeting forms a disk structure. The two surfaces of the sheeting with the greatest surface area are called the faces of the sheeting.

Solution: As used in this disclosure, a solution is a uniform mixture of two or more compounds in a liquid phase. The major component selected from the two or more compounds that forms the solution is called the solvent. The components remaining in the two or more compounds are called the solute. A polar solvent is a solvent formed from polar molecules. A non-polar solvent is a solvent formed from non-polar molecules. The rule of thumb that "like dissolves like" states that: a) solutes formed from polar molecules will dissolve in polar solvents but will not dissolve in non-polar solvents; and, b) solutes formed from non-polar molecules will dissolve in non-polar solvents but will not dissolve in polar solvents. Use Polarity Polar Molecule and non-polar molecule Surface Filter: As used in this disclosure, a surface filter is a type of filter wherein the fluid is passed through a surface or membrane, such as a screen or paper that allows for the passage of the fluid but blocks the passage of larger particles that may be suspended in the fluid. The construction of a surface filter would allow for the passage of the fluid through several filter surfaces in one filtration unit.

Textile: As used in this disclosure, a textile is a material that is woven, knitted, braided or felted. Synonyms in common usage for this definition include fabric and cloth. The two surfaces of the textile with the greatest surface area are called the faces of the textile.

Topical: As used in this disclosure, topical is an adjective that is associated with a pharmacologically active media. Topical indicates that the pharmacologically active media is applied directly to the skin.

Virus: As used in this disclosure, a virus is a biological entity that is capable of reproduction but does not have the biological mechanisms to generate the energy for replication. A virus "infects" a host cell and uses the biochemical biological processes of the host cell as the energy source that allows the virus to replicate. Because the virus is incapable of independently generating the biochemical energy necessary for reproduction, the traditional view is that viruses are not a form of life. All viruses comprise a nucleic acid structure and a protein shell. The nucleic acid structure is genetic material that is selected from the group consisting of RNA and DNA. The nucleic acid structure is enclosed within the protein shell. The protein shell is known as the capsid. The proteins of the capsid are encoded by the nucleic acid structure. The capsid: a) protects the nucleic acid structure when the virus is dormant; and, b) attaches the virus to a biological structure of a host cell that is suitable to support the replication of the virus. More evolved viruses further comprise an envelope. The envelope is a lipid based structure that is similar to a cell membrane. By similar to the cell membrane is meant that: a) the envelope is formed with a bilayer lipid structure similar to a cell membrane; and, b) the envelope will display membrane protein structures to its environment in a similar to a cell membrane. The envelope encloses the capsid and the nucleic acid structure. In this disclosure, a virus formed with an envelope is referred to as an evolved virus. The term virus can refer to viruses with or without an envelope.

Webbing: As used in this disclosure, a webbing is strong, close woven or knitted fabric that is used for straps or belting. As used in this disclosure, webbing is a fully formed material that is only cut to length for use. Webbing is not formed by cutting broader materials into strips. Webbings have tensile strength but are too flexible to provide compressive strength and are not suitable for use in pushing objects. The shape of a webbing is approximated by a rectangular disk shape. The two surfaces of a webbing with the greatest surface area are called the faces of the webbing.

With respect to the above description, it is to be realized that the optimum dimensional relationship for the various components of the invention described above and in FIGS. 1 through 5 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. A face mask impregnated with medicine comprising a mask structure, a fastening structure, and a medical coating;

wherein the face mask impregnated with medicine is configured for use with a patient;

wherein the fastening structure is configured to attach the mask structure to the patient;

wherein the medical coating is a pharmacologically active media that is configured to treat medical conditions that are caused or exacerbated by the mask structure;

wherein the face mask impregnated with medicine is configured to cover the mouth and nose on the face of the patient;

wherein the face mask impregnated with medicine is configured to filter the air that is inhaled and exhaled by the patient;

wherein the mask structure is configured to filter the air that is inhaled and exhaled by the patient;

wherein the medical coating is selected from the group consisting of: a) a pharmacologically active media with a primary chemical structure of (all-trans)-3,7-dimethyl-9-(2,6,6-trimethyl-1-cyclohexene-1-yl)-2,4,6,8-nonatetraenoic acid (CAS 302-79-4); and, b) a pharmacologically active media with a primary chemical structure of α-[[(1.1-Dimethylethyl)amino]methyl]-4-hydroxy-1,3-benzenedimethanol (CAS 18559-94-9).

2. A face mask impregnated with medicine comprising a mask structure, a fastening structure, and a medical coating;

wherein the fastening structure attaches to the mask structure;

wherein the medical coating is applied to the mask structure;

wherein the mask structure comprises an inner layer, a filter layer, and an outer layer;

wherein the filter layer is sandwiched between the inner layer and the outer layer;

wherein the medical coating is configured to be applied to the face of the inner layer that is proximal to the face of the patient;

wherein the medical coating is selected from the group consisting of: a) a pharmacologically active media with a primary chemical structure of (all-trans)-3,7-dimethyl-9-(2,6,6-trimethyl-1-cyclohexene-1-yl)-2,4,6,8-nonatetraenoic acid (CAS 302-79-4); and, b) a pharmacologically active media with a primary chemical structure of α-[[(1.1-Dimethylethyl)amino]methyl]-4-hydroxy-1,3-benzenedimethanol (CAS 18559-94-9).

3. The face mask impregnated with medicine according to claim 2, wherein the face mask impregnated with medicine is adapted for use with a patient;

wherein the face mask impregnated with medicine is configured to cover the mouth and nose on the face of the patient;

wherein the face mask impregnated with medicine is configured to filter the air that is inhaled and exhaled by the patient.

4. The face mask impregnated with medicine according to claim 3, wherein the mask structure is configured to filter the air that is inhaled and exhaled by the patient;

wherein the fastening structure is configured to attach the mask structure to the patient;

wherein the medical coating is a pharmacologically active media.

5. The face mask impregnated with medicine according to claim 4, wherein the mask structure is a textile based structure;

wherein the mask structure is a composite textile.

6. The face mask impregnated with medicine according to claim 5, wherein the medical coating is a pharmacologically active media;

wherein the medical coating is formed as a gas permeable structure;

wherein the medical coating is configured to be selected from the group consisting of a topically applied pharmacologically active media and an inhaled pharmacologically active media.

7. The face mask impregnated with medicine according to claim 6, wherein the fastening structure is a mechanical structure;

wherein the fastening structure is configured to attach to the mask structure;

wherein the fastening structure is configured to secure the mask structure to the patient;

wherein the fastening structure is an elastic structure.

8. The face mask impregnated with medicine according to claim 7, wherein the inner layer is one selected from the group consisting of: a sheeting structure; a textile based structure; the composite prism structure of the mask structure that is proximal to the face of the patient; and a gas permeable structure.

9. The face mask impregnated with medicine according to claim 8, wherein the inner layer is an absorbent structure;

wherein the outer layer is a sheeting structure;

wherein the outer layer is a textile based structure;

wherein the outer layer is the layer of the composite prism structure of the mask structure that is distal from the face of the patient;

wherein the outer layer is a gas permeable structure;

wherein the outer layer is an absorbent structure.

10. The face mask impregnated with medicine according to claim 9, wherein the filter layer is a sheeting structure;

wherein the filter layer is a textile based structure;

wherein the filter layer is a gas permeable structure;

wherein the filter layer forms a filter.

11. The face mask impregnated with medicine according to claim 10, wherein the filter layer is configured to form an N95 filter.

12. The face mask impregnated with medicine according to claim 11, wherein the medical coating is selected from the group consisting of: a) a pharmacologically active media with a primary chemical structure of (all-trans)-3,7-dimethyl-9-(2,6,6-trimethyl-1-cyclohexene-1-yl)-2,4,6,8-nonatetraenoic acid (CAS 302-79-4); and, b) a pharmacologically active media with a primary chemical structure of α-[[(1,1-Dimethylethyl)amino]methyl]-4-hydroxy-1,3-benzenedimethanol (CAS 18559-94-9).

13. The face mask impregnated with medicine according to claim 11, wherein the medical coating is an (all-trans)-3,7-dimethyl-9-(2,6,6-trimethyl-1-cyclohexene-1-yl)-2,4,6,8-nonatetraenoic acid (CAS 302-79-4);

wherein the (all-trans)-3,7-dimethyl-9-(2,6,6-trimethyl-1-cyclohexene-1-yl)-2,4,6,8-nonatetraenoic acid (CAS 302-79-4) is configured to be topically applied to the patient;

wherein the (all-trans)-3,7-dimethyl-9-(2,6,6-trimethyl-1-cyclohexene-1-yl)-2,4,6,8-nonatetraenoic acid (CAS 302-79-4) is provided in a formulation comprising a lipid.

14. The face mask impregnated with medicine according to claim 11, wherein the medical coating is a 1,3-benzenedimethanol, α1-[[(1,1-dimethylethyl)amino]methyl]-4-hydroxy-(CAS 18559-94-9);

wherein the 1,3-benzenedimethanol, α1-[[(1,1-dimethylethyl)amino]methyl]-4-hydroxy-(CAS 18559-94-9) is inhaled by the patient.

* * * * *